United States Patent [19]
Nakamura et al.

[11] Patent Number: 5,614,943
[45] Date of Patent: Mar. 25, 1997

[54] DISSIMILAR ENDOSCOPES USABLE WITH A COMMON CONTROL UNIT

[75] Inventors: Kazunari Nakamura, Hino; Katsuyuki Saito, Hachioji; Hiroyuki Sasa, Hachioji; Yoshihiro Okada, Hachioji; Hisao Yabe, Hachioji; Shigeru Nakajima, Hachioji; Seiji Yamaguchi, Hachioji, all of Japan

[73] Assignee: Olympus Optical Co., Ltd., Tokyo, Japan

[21] Appl. No.: 428,833

[22] Filed: Apr. 25, 1995

Related U.S. Application Data

[63] Continuation of Ser. No. 232,425, Apr. 21, 1994, abandoned, which is a continuation of Ser. No. 986,029, Dec. 4, 1992, abandoned.

[30] Foreign Application Priority Data

Dec. 19, 1991 [JP] Japan ................................. 3-337135
Dec. 26, 1991 [JP] Japan ................................. 3-345543

[51] Int. Cl.$^6$ ........................... A61B 1/04; H04N 7/18
[52] U.S. Cl. ........................................................ 348/72
[58] Field of Search ......................... 358/98; 128/6, 128/4; 348/72, 65, 74, 75, 458

[56] References Cited

U.S. PATENT DOCUMENTS

| | | | |
|---|---|---|---|
| 4,539,586 | 9/1985 | Danna et al. | 358/98 |
| 4,759,346 | 7/1988 | Nakajima | 358/98 |
| 4,816,909 | 3/1989 | Kimura et al. | |
| 4,853,773 | 8/1989 | Hibino et al. | |
| 4,855,819 | 8/1989 | Hibino et al. | |
| 4,891,695 | 1/1990 | Uchikubo et al. | |
| 4,894,715 | 1/1990 | Uchikubo et al. | 348/65 |
| 4,926,258 | 5/1990 | Sasaki et al. | 358/98 |
| 4,979,497 | 12/1990 | Matsura et al. | 348/65 |
| 5,006,928 | 4/1991 | Kawajiri et al. | 348/70 |
| 5,043,811 | 8/1991 | Yasuhiro | 348/458 |
| 5,212,550 | 5/1993 | Park | 348/458 |
| 5,229,853 | 7/1993 | Myers | 348/458 |
| 5,233,416 | 8/1993 | Inoue | 358/98 |
| 5,258,834 | 11/1993 | Tsuji et al. | 348/71 |
| 5,309,227 | 5/1994 | Inoue | 348/71 |
| 5,335,662 | 8/1994 | Kimura et al. | 128/662.03 |

FOREIGN PATENT DOCUMENTS

| | | | |
|---|---|---|---|
| 62-54215 | 3/1987 | Japan | 358/98 |
| 63-260527 | 10/1988 | Japan. | |

*Primary Examiner*—Tommy P. Chin
*Assistant Examiner*—Bryan S. Tung
*Attorney, Agent, or Firm*—Armstrong, Westerman, Hattori, McLeland & Naughton

[57] ABSTRACT

An endoscope system comprises an endoscope control unit provided with an image signal generating circuit for signal processing an image pickup signal from an endoscope to generate an image signal, and a drive-signal generating circuit for generating a drive signal for driving an image pickup element provided on the endoscope; a first endoscope capable of being connected to the endoscope control unit and provided with a first image pickup element for image pickup of a subject image; a second endoscope capable of being connected to the endoscope control unit and provided with a second image pickup element different from the first image pickup element, for picking up the subject image; and a signal rationalizing circuit for rationalizing a form of a signal exchanged between at least one of the first endoscope and the second endoscope, and the endoscope control unit.

2 Claims, 14 Drawing Sheets

5,614,943

DISSIMILAR ENDOSCOPES USABLE WITH A COMMON CONTROL UNIT

This application is a continuation of application Ser. No. 08/232,425 filed Apr. 21, 1994, now abandoned, which was a continuation of application Ser. No. 07/986,029 filed Dec. 4, 1992, now abandoned.

BACKGROUND OF THE INVENTION

1. Field of the Invention

The present invention relates to an endoscope system capable of taking measures against a plurality of electronic endoscopes provided with image pickup means different in specification from one other.

2. Description of the Related Art

In recent years, an electronic endoscope (referred also to as "an electronic scope" or referred simply as "a scope") which uses a solid state image pickup element such as a charge coupled device (hereinafter referred to as "a CCD") or the like, as an image pickup means has widely been used.

In such an electronic scope, observing parts also digress or ramify complicatedly, and it has been further found that a forward end portion of the endoscope is further reduced in diameter, in keeping with development of recent endoscope medical science. For example, for a thick organ part such as a large intestine or the like and for a thin organ part such as a trachea or the like, diameters of permitted or admitted endoscopes are different from one other. Accordingly, since the solid state image pickup element of a picture-element arrangement matched with the thick organ part is large in size, the endoscope for the thin organ cannot be arranged. Conversely, since the solid state image pickup element matched with the thin organ part is small in size with respect to the diameter of the endoscope for the thick organ, a surplus space is generated. This results in waste of a part which is originally an image pickup surface. This is not efficient. Accordingly, an endoscope having the picture-element arrangement taking measures against the observing parts has been required or necessitated.

In a conventional video camera or the like, for example, a picture element size or the number of longitudinal and lateral picture elements of the image pickup element is only a single type or kind, but there is no arrangement which uses image pickup elements equal to or more than two kinds. Further, also in the electronic scope, a, used solid state image pickup element has conventionally been limited to a single kind or type.

In an apparatus which uses the solid state image pickup element, in a case where specifications of the arranged solid state image pickup elements (the number of picture elements or the like, for example) are different from each other, driving of the solid state image pickup elements and signal processing of an output are required to be executed in accordance with the kinds or types of the respective solid state image pickup elements.

Nevertheless, since a drive circuit for the solid state image pickup element and a signal processing circuit are fixed, the conventional electronic endoscope apparatus has such a disadvantage that only an electronic scope can be used which uses the solid state image pickup elements which are the same in type as each other and the same in specification as each other.

In order to solve the above-discussed disadvantage or problem, there is an endoscope apparatus, for example, which has been proposed in Japanese Patent Laid-Open No. SHO 63-260527, in which a plurality of camera control units (CCU) taking measures respectively against electronic scopes different in kind from each other are prepared, and these plurality of camera control units are changeably mounted within a video process unit, whereby a different electronic scope can be used.

In a case of the endoscope apparatus disclosed in Japanese Patent Laid-Open No. SHO 63-260527, however, the existent endoscope apparatus, that is, the conventional endoscope apparatus in which the video process unit is such that the plurality of camera control units cannot be mounted exchangeably and cannot be adapted or adjusted. Moreover, since the camera control unit can be mounted exchangeably, there is a problem that the video process unit is enlarged in size.

Furthermore, U.S. Pat. No. 4,816,909 discloses an endoscope system in which, for the purpose of providing an electronic endoscope apparatus taking measures against a plurality of scopes which consist of solid state image pickup elements different in number of picture elements from each other, a detecting circuit for the scope is provided on a body apparatus, drive pulses of the solid state image pickup element and the signal processing circuit are switched to an adequate value by a detecting signal from the detecting circuit.

Since, however, the apparatus disclosed in U.S. Pat. No. 4,816,909 is so arranged as to take measures against an electronic scope which is different in number of picture elements of the solid state image pickup element from the first time, the arrangement of the signal processing circuit is complicated in structure. Further, there is such a disadvantage that a user must use the signal processing circuit provided with surplus functions, in a case also where the electronic endoscope apparatus is used only for a specific scope, for example.

SUMMARY OF THE INVENTION

It is an object of the invention to provide an endoscope system which can select a system arrangement in accordance with a scope which is used by a user, and which can take measures against specifications of the scopes different from each other.

It is another object of the invention to provide an endoscope system in which a plurality of electronic endoscopes provided with solid state image pickup elements different in kind or type from each other is capable of being connected to a single camera control unit so that the camera control units are commonly used so as to be capable of taking measures against a plurality of electronic endoscopes different in type from each other.

Another object of the invention is to provide an endoscope system in which a system suitable for a used scope can easily be arranged. It is not required or unnecessary to beforehand provide a driver taking measures against all of CCDs. An image-signal processing section is used commonly so as to be capable of taking measures against the CCDs different in specification from each other, and the system can be arranged with a low price or at low cost.

It is still another object of the invention to provide an endoscope system in which a system arrangement can easily be altered or changed in accordance with types of a used electronic endoscope.

It is another object of the invention to provide an endoscope system in which an existing camera control unit and a plurality of types of endoscopes are combined with each other so as to be capable of easily arranging a system which is capable of using a plurality of types of endoscopes different in specification from each other.

According to the invention, there is provided an endoscope system comprising an endoscope control unit provided with image-signal generating means for signal-processing an image pickup signal from an endoscope to generate an image signal, and drive-signal generating means for generating a drive signal for driving image pickup means provided on the endoscope; a first endoscope capable of being connected to the endoscope control unit and provided with first image pickup means for image-picking-up a subject image; a second endoscope capable of being connected to the endoscope control unit and provided with second image pickup means different from the first image pickup means, for image-picking-up the subject image; and signal rationalizing means for rationalizing a form of a signal exchanged between at least one of the first endoscope and the second endoscope, and the endoscope control unit.

These objects and advantages of the present invention will become sufficiently apparent from the following explanation.

BRIEF DESCRIPTION OF THE DRAWINGS

FIGS. 1(a) to 3 relate to a first embodiment of the invention, FIGS. 1(a) and 1(b) being block diagrams showing an arrangement of an endoscope system;

FIG. 3 is a block diagram showing an arrangement of a common CCU;

FIG. 6 is an arrangement view showing an arrangement of an endoscope provided with a CCD which is different in type or kind from the endoscope illustrated in FIG. 5;

FIG. 7 is a block diagram showing an arrangement of drive-signal converting means;

FIG. 8 is a block diagram showing an arrangement of output-format converting means;

FIG. 14 is a block diagram showing an internal arrangement of the endoscope system illustrated in FIG. 13;

FIG. 18 is a block diagram showing an arrangement of an endoscope system in a case where another endoscope different from the endoscope illustrated in FIG. 17 is used;

FIG. 20 is a block diagram showing the arrangement of the endoscope system in a case where another endoscope different from the endoscope illustrated in FIG. 19 is used.

DETAILED DESCRIPTION OF THE PREFERRED EMBODIMENTS

FIGS. 1(a) to 3 show a first embodiment of the invention.

Figure 1A:
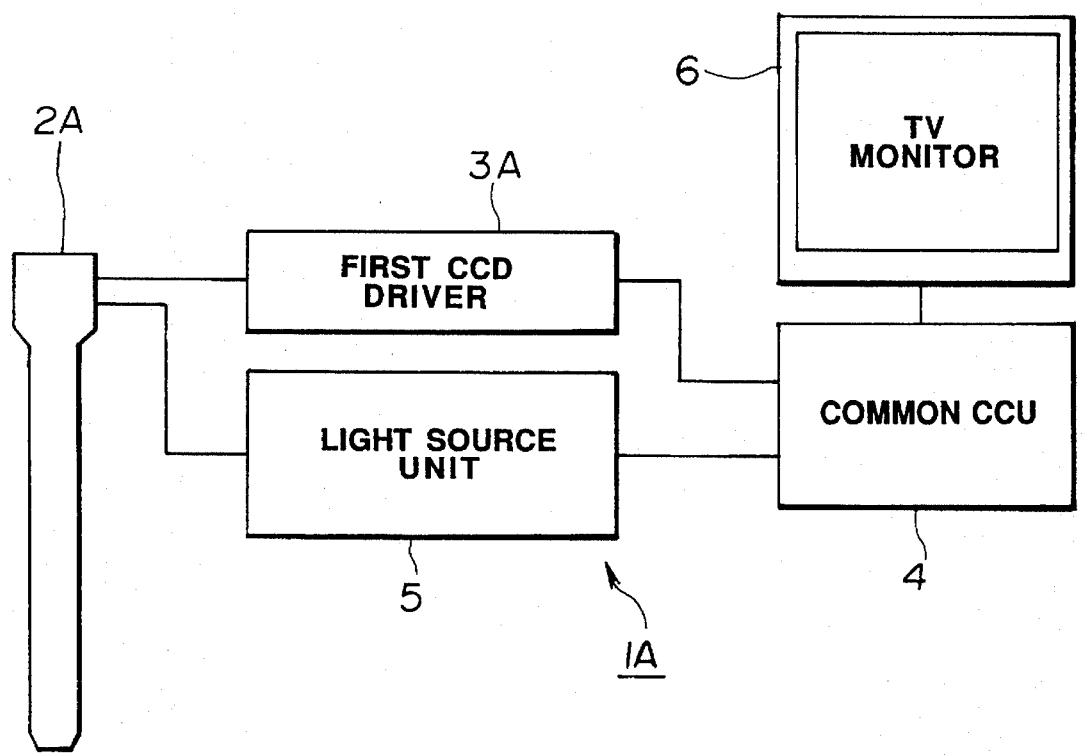
Figure 1B:
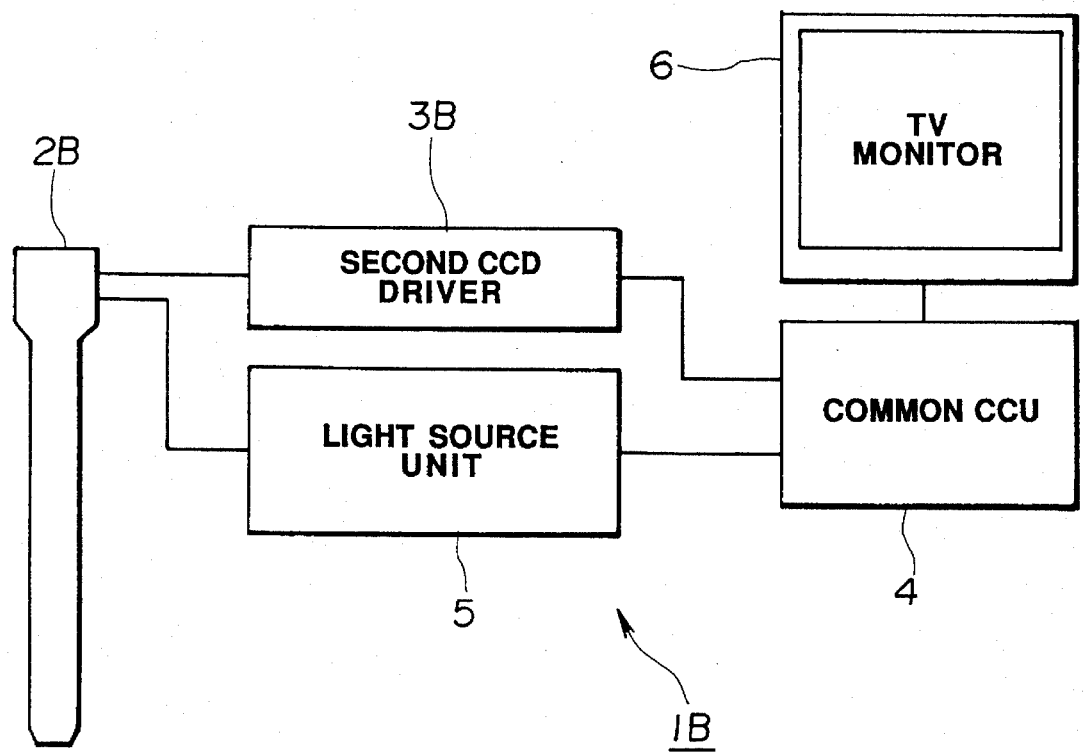

The first embodiment is an example of an apparatus capable of using a pair of electronic endoscopes 2A and 2B different in specification from each other, and a system arrangement thereof is brought to that illustrated in FIG. 1(a) or FIG. 1(b) according to used electronic endoscopes 2A and 2B.

A system 1A illustrated in FIG. 1(a) comprises the first electronic endoscope 2A provided at a tip or a forward end thereof with a CCD (not shown) of high resolution for a digestive organ or alimentary canal, a first CCD driver 3A for generating various kinds of drive signals for driving the CCD of high resolution and for signalizing the drive signals to image signals of a constant or determined standard or specification, a common CCU (camera control unit) 4 for executing signal processing with respect to the image signals of the predetermined standard outputted from the CCD driver 3A to generate a standard image signal, a light source unit 5 for controlling a quantity of illuminating light by a modulated-light signal due to the common CCU unit 4 to execute illumination of a subject, and a TV monitor 6 for displaying the standard image signal due to the common CCU 4. In this connection, the endoscope and the CCU in the embodiment of the invention are arranged by ones of a surface successive type.

On the other hand, in a system 1B illustrated in FIG. 1(b), the second endoscope 2B provided at a forward end thereof with a small-sized or miniaturized CCD (not shown) for a broncho (bronchus) and a second CCD driver 3B for generating a drive signal for the miniaturized CCD and for signalizing the drive signal to an image signal of a predetermined standard are so arranged as to be provided with constitutional elements which are different from those of the system 1A illustrated in FIG. 1(a) but which are common to those of the system 1A in other respects.

Figure 2A:
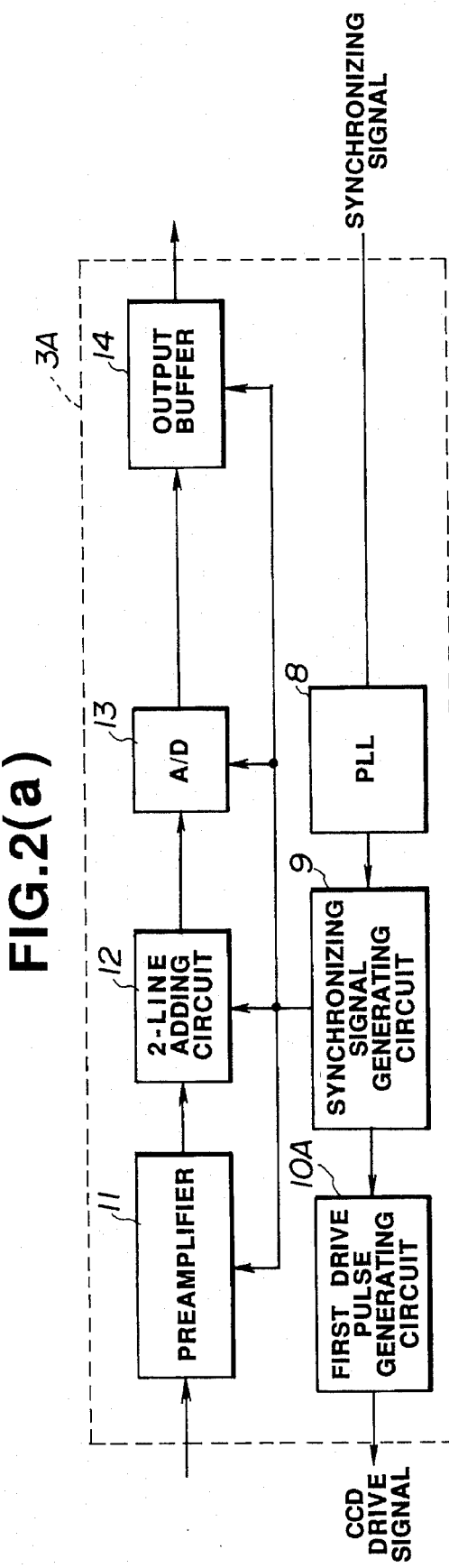
FIGS. 2(a) and 2(b) are block diagrams showing an arrangement of a CCD driver.

The first CCD drive 3A is arranged as shown in FIG. 2(a). The first CCD driver 3A is provided with a PLL circuit 8 for synchronizing an internal signal by a synchronizing signal from the common CCU unit 4, a synchronizing-signal generating circuit 9 for synchronizing the common CCU 4 and a phase with each other by the PLL circuit 8 to generate a synchronizing signal of signals within the CCD driver 3A, and a first drive-pulse generating circuit 10A for generating a drive signal exclusive for the high picture-element CCD provided on the first electronic endoscope 2A on the basis of the signal generated by the synchronizing-signal generating circuit 9.

Moreover, the first CCD driver 3A is provided with a preamplifier 11 for removing a noise component from the image signal from the high picture-element CCD driven by the first drive-pulse generating circuit 10A to amplify the image signal. Since the high picture-element CCD has many picture elements, simultaneous reading of two (2) lines is executed in order to execute high-speed reading. For this reason, a 2-line adding circuit 12 is provided which adds in two lines outputs from the preamplifier 11 to each other. An A/D converter 13 for A/D-converting an output from the 2-line adding circuit 12 and an output buffer 14 for outputting an output from the A/D converter 13 to the common CCU 4 are provided. An image signal of a predetermined standard is outputted from the output buffer 14 and is processed by the common CCU 4, whereby it is possible to generate a standard image signal.

Figure 2B:
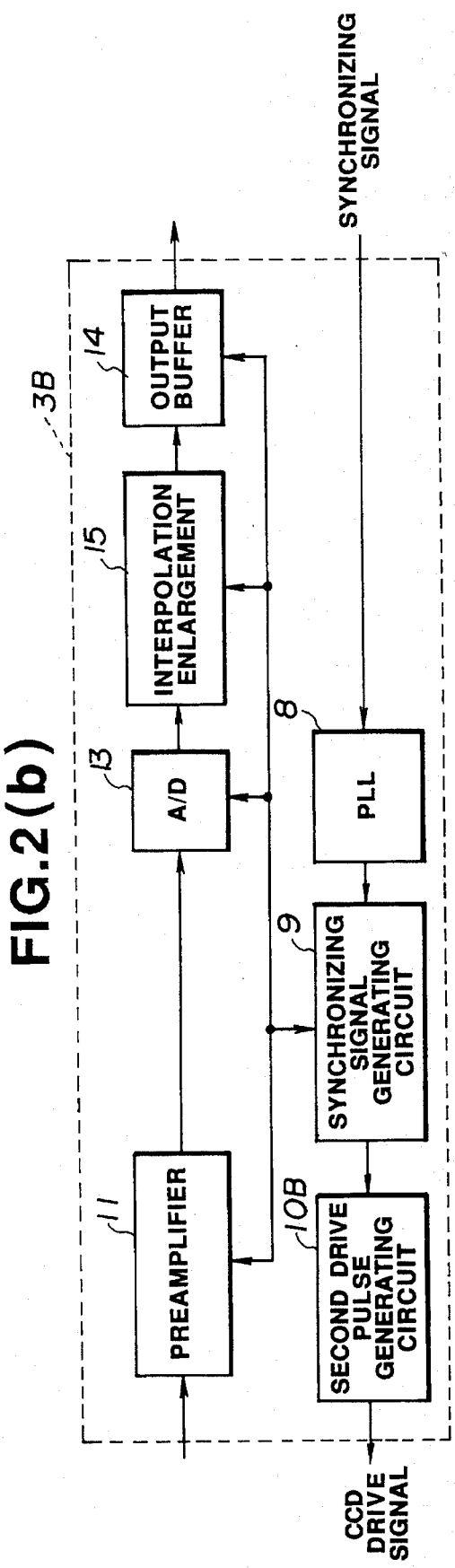

On the other hand, the second CCD driver 3B is arranged as illustrated in FIG. 2(b). Points different from the first CCD driver 3A will be described.

A synchronizing-signal generating circuit 9 for generating a synchronizing signal of signal within the second CCD driver 3B, and a drive-pulse generating circuit 10B for generating a drive signal exclusive for the miniaturized CCD provided on the second electronic endoscope 2B, on the basis of the synchronizing signal from the synchronizing-signal generating circuit 9 are provided on an output side of a PLL circuit 8. Furthermore, an interpolation enlargement circuit 15 for interpolation-processing the image signal read from the miniaturized CCD to enlarge the image signal are provided on an output side of an A/D converter 13. In this connection, since the CCD driver 3B is one taking measures against a CCD small in size and having a fewer number of picture elements, 2-line reading is not executed and, accordingly, the 2-line adding circuit 12 is not provided. In other respects, the CCD driver 3B is similar in arrangement to the first CCD driver 3A.

Figure 3:
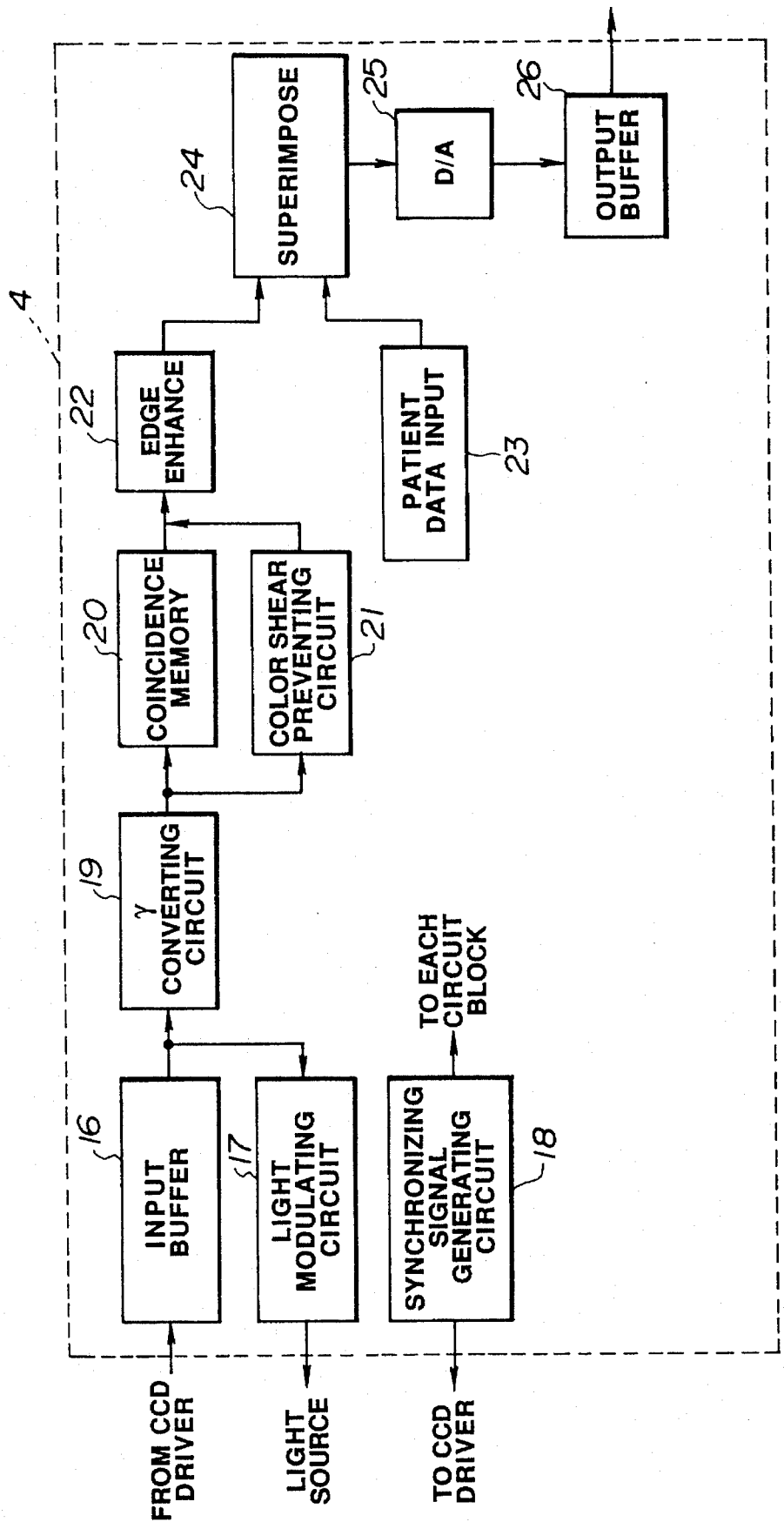

An arrangement of the common CCU 4 will next be shown in FIG. 3.

The common CCU 4 is provided with an input buffer 16 for buffering digital signals outputted from the various kinds of CCD driver 3A or 3B, and a γ converting circuit 19 for γ-converting the digital signal that is an output from the input buffer 16. Further arranged are a modulated-light circuit 17 for computing an image-signal level on the basis of the Image signal from the input buffer circuit 16 to compute a control signal for modulated light, and a synchronizing-signal generating circuit 18 for generating timing signals of the common CCU 4 and the CCD drivers 3A and 3B.

Moreover, the common CCU 4 has a coincidence memory 20 receiving an output from the γ-converting circuit 19 for coinciding a color signal read out in a time-series manner, and a color-smear preventing circuit 21 for reducing a color smear generated by movement of the subject or the endoscope. Furthermore, the common CCU 4 is provided with an edge enhance circuit 22 for emphasizing an edge portion of the image signal outputted from the coincidence memory 20 to thereby increase sharpness, a patient-data input circuit 23 for inputting data of a patient observed, and a superimpose circuit 24 for synthesizing or composing the inputted patient data and the observed image with each other. A D/A converter 25 for converting an image composed by the superimpose circuit 24 to an analog image signal so as to be capable of being observed, and an output buffer circuit 26 for outputting an image signal to the TV monitor 6 are provided.

Operation of the first embodiment will be described below.

Since the first electronic endoscope 2A is provided with the CCD of high resolution, an outer diameter of the scope is thickened or increased. However, since a fine or minute lesion is capable of being found, the first electronic endoscope 2A is used for a digestive organ. The electronic endoscope 2A is driven by the exclusive CCD driver 3A executing simultaneous reading-out of two (2) lines, because the number of picture elements is many because of high resolution.

As shown in FIG. 2(a), the CCD driver 3A applies PLL at the PLL circuit 8 by the synchronizing signal from the common CCU 4 to synchronize a synchronizing signal generated by the inside synchronizing-signal generating circuit 9 with the common CCU 4. Various circuits of the CCD driver 3A are synchronized with each other on the basis of the synchronizing signal from the synchronizing-signal generating circuit 9.

The drive-pulse generating circuit 10A generates a drive signal exclusive for the high resolution CCD, on the basis of the synchronizing signal of the synchronizing-signal generating circuit 9, to thereby drive the CCD which is arranged within the electronic scope 2A.

The image signal from the CCD driven by the drive-pulse generating circuit 10A is executed in noise removal by the preamplifier 11, and is amplified thereby. The output from the preamplifier 11 is such that image signals corresponding to two (2) lines are composed with each other by the 2-line adding circuit 12. The 2-line adding circuit 12 is provided for reproducing or reappearing the image signal read out in division of information corresponding to one or single line into two lines, for the purpose of executing high-speed reading, because the electronic endoscope 2A has many picture elements. The image signal compounded or synthesized by the 2-line adding circuit 12 is converted into digital data by the A/D converter 13 and, subsequently, is outputted from the output buffer circuit 14 to the common CCU 4.

On the other hand, the CCD driver 3B drives the second electronic endoscope (broncho endoscope) 2B by the drive-pulse generating circuit 10B for generating the drive signal exclusive for the miniaturized CCD. The image signal from the CCD is amplified by the preamplifier 11 similarly to the CCD driver 3A.

Differentiated from the CCD driver 3A, an adding circuit of 2 (two) lines is not required because the electronic endoscope 2B has fewer picture elements. Accordingly, the output from the preamplifier 11 is converted to digital data by the A/D converter 13. The image signal of the miniaturized CCD which has been converted to the digital data is small in display area as compared with the high resolution CCD, because the number of picture elements is less. Accordingly, in order to properly arrange the display areas, interpolation and enlargement is executed by the interpolation enlargement circuit 15 to arrange the display areas and, subsequently, the image signal from the miniaturized CCD is outputted to the common CCU 4 as the image signal of a predetermined standard (a digital image signal synchronized with the synchronizing signal from the common CCU unit 4, for example) from the output buffer 14.

The common CCU 4 executes γ conversion in which the image signal digitized from the exclusive CCD driver 3A or 3B is received by the input buffer 16 and is displayed on the TV monitor 6 by the γ-converting circuit 19. An RGB image signal inputted in a time-series manner is coincided by the coinciding memory 20.

Here, the endoscope of a surface successive system forms one set of images on the basis of the RGB image signal which is picked up in a time-series manner. Accordingly, since a color shift occurs if the subject is moved, the color shift is corrected by the color-shift correcting circuit 21. The image signal in which the color shift is corrected emphasizes an edge by the edge enhance circuit 22 to improve sharpness.

The patient data inputted from the patient-data input circuit 23 and the image executed in enhance of the edge by the edge enhance circuit 22 are synthesized with each other by the superimpose circuit 24. The endoscope image which is synthesized in image plane by the superimpose circuit 24 is converted into the analog signal by the D/A converter 25, and is outputted to the TV monitor 6 through the output buffer 26.

As described above, division is made into the exclusive circuits corresponding respectively to various kinds of CCDs different in specification from each other and the circuit common to the various CCDs. Thus, only replacement of the CCD drivers corresponding respectively to the various kinds of CCDs makes it possible to easily arrange the endoscope system in which various kinds of exclusive CCDs are capable of being used without being brought to a circuit arrangement corresponding to all of the exclusive CCDs classified respectively for adaptive parts such as a digestive organ, a bronchus and the like.

Further, the endoscope system for observing a broncho can be arranged by the small driver 3B exclusive for the CCD and the common CCU 4, and the endoscope for observing a digestive organ is arranged by the driver 3A exclusive for the high resolution CCD and the common CCU unit 4. Accordingly, it is possible to select or choose a system arrangement in accordance with a scope which is intended to be used by the user, and it is possible to easily arrange a system which is adequate or suitable for the used scope. Moreover, it is not required beforehand to provide the driver corresponding to all the CCDs such that various kinds of CCDs are capable of being used, and the image-signal processing section can commonly be used also for scopes different in specification from each other. Thus, it is possible to arrange the system cheaply or at low cost.

Furthermore, it is possible to easily change the system arrangement in a case where the kinds or types of the used electronic endoscope increases.

In connection with the above, the output signal from the exclusive CCD driver may not be digital data, but may be analog data.

Further, the various circuit arrangements of the exclusive CCD driver and the common CCU unit should not be limited to the aforesaid arrangement example. The arrangement may be such that a circuit peculiar to the various CCDs is provided on the CCD driver, and a processing circuit capable of being used commonly is arranged as a common CCU.

Figure 4:
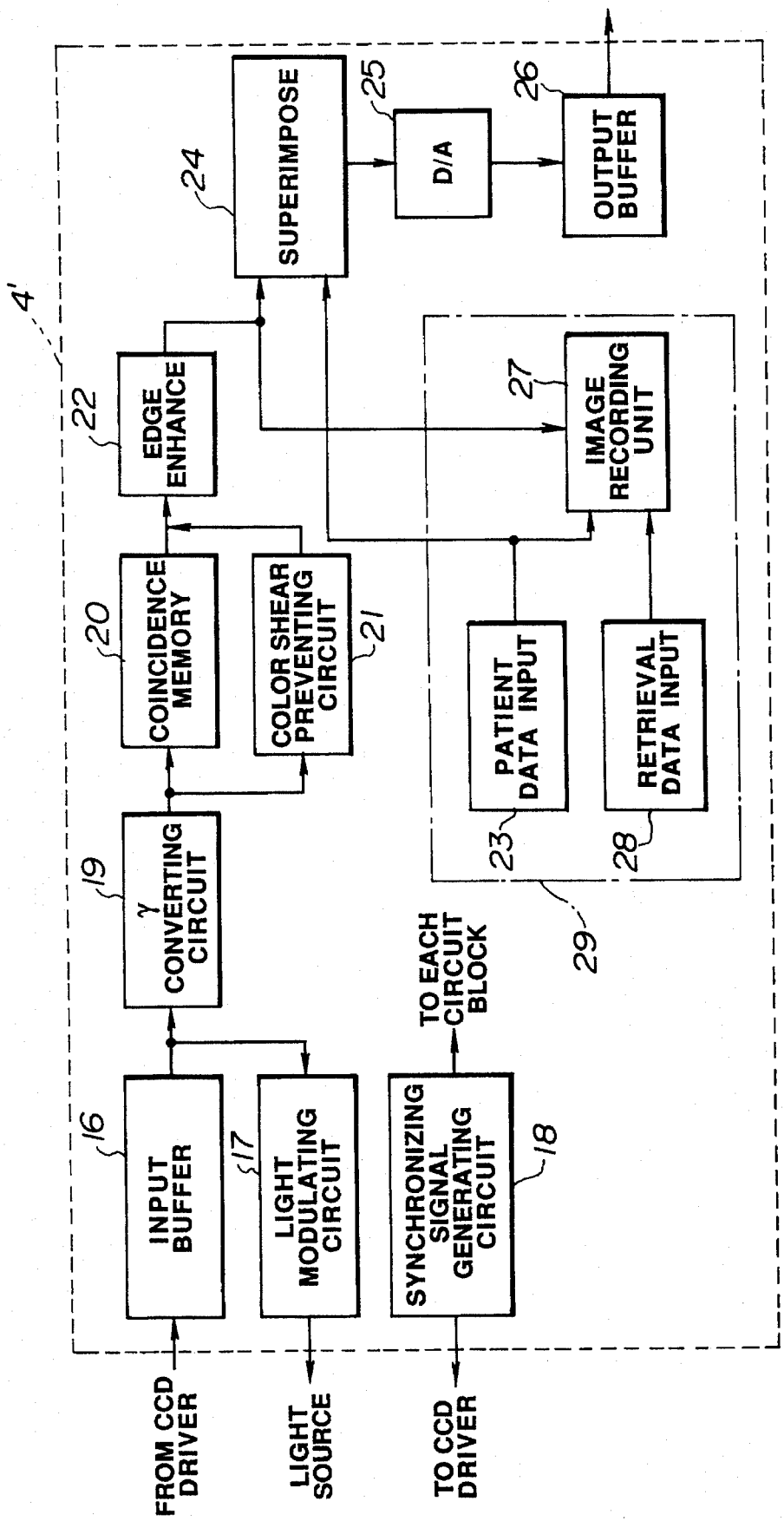
FIG. 4 is a block diagram showing an arrangement of a common CCU in a second embodiment of the invention.

FIG. 4 shows an arrangement of a common CCU in a second embodiment of the invention.

The second embodiment is a modification of the common CCU of the first embodiment. A CCU 4' of the second embodiment has an image recording unit 27 for recording an image signal edge-enhanced by an edge enhance circuit 22, and a retrieval-data input circuit 28 for executing retrieving of a recorded image, in addition to the common CCU 4 illustrated in FIG. 3.

Moreover, a superimpose circuit 24 is adapted to synthesize the image signal from the image recording unit 27 or the edge enhance-circuit 22 and the patient data from the patient-data input circuit 28 with each other. That is, the present embodiment is one in which an image filing unit 29 having the image recording unit 27, a patient-data input circuit 23, and the retrieval-data input circuit 28 is executed commonly. Other arrangements are the same as those of the first embodiment.

Operation of the second embodiment of the Invention will next be described.

At observation of a part to be inspected, an image signal outputted from the edge enhance circuit 22 is synthesized with patient data inputted from the patient-data input circuit 23 by the superimpose circuit 24, and is outputted to a TV monitor 6, so that an endoscope image is displayed on the monitor. On the other hand, at recording of the observed image, an image signal from the edge enhance circuit 22 is recorded on the image recording unit 27 together with the patient data. In a case where it is desired that the recorded data are played back or reproduced and are observed, retrieval data are inputted from the retrieval-data input circuit 28, and the image data recorded on the image recording unit 27 are retrieved so that an objective image signal is outputted from the image recording unit 27.

The second embodiment is common also in the image filing unit 29 in addition to the arrangement similar to the first embodiment. Accordingly, an attempt can be made to further simplify the circuit, and it is possible to arrange the system at low cost. Further, since the digital data are recorded as they are, filing high in image quality is also possible.

In connection with the above, the image filling section and the CCU may be formed separately.

Moreover, the first and second embodiments should not be limited to a system which uses illumination and image pickup means of surface successive type, but may be applied also to a system of coincidence or simultaneous type, or may be an arrangement of a system in which a surface successive type and a simultaneous type exist in mixture.

A third embodiment of the invention is shown in FIGS. 5 to 8.

An endoscope system 31 according the third embodiment is an example which is capable of using a plurality of endoscopes which are different in arrangement from each other.

Figure 5:
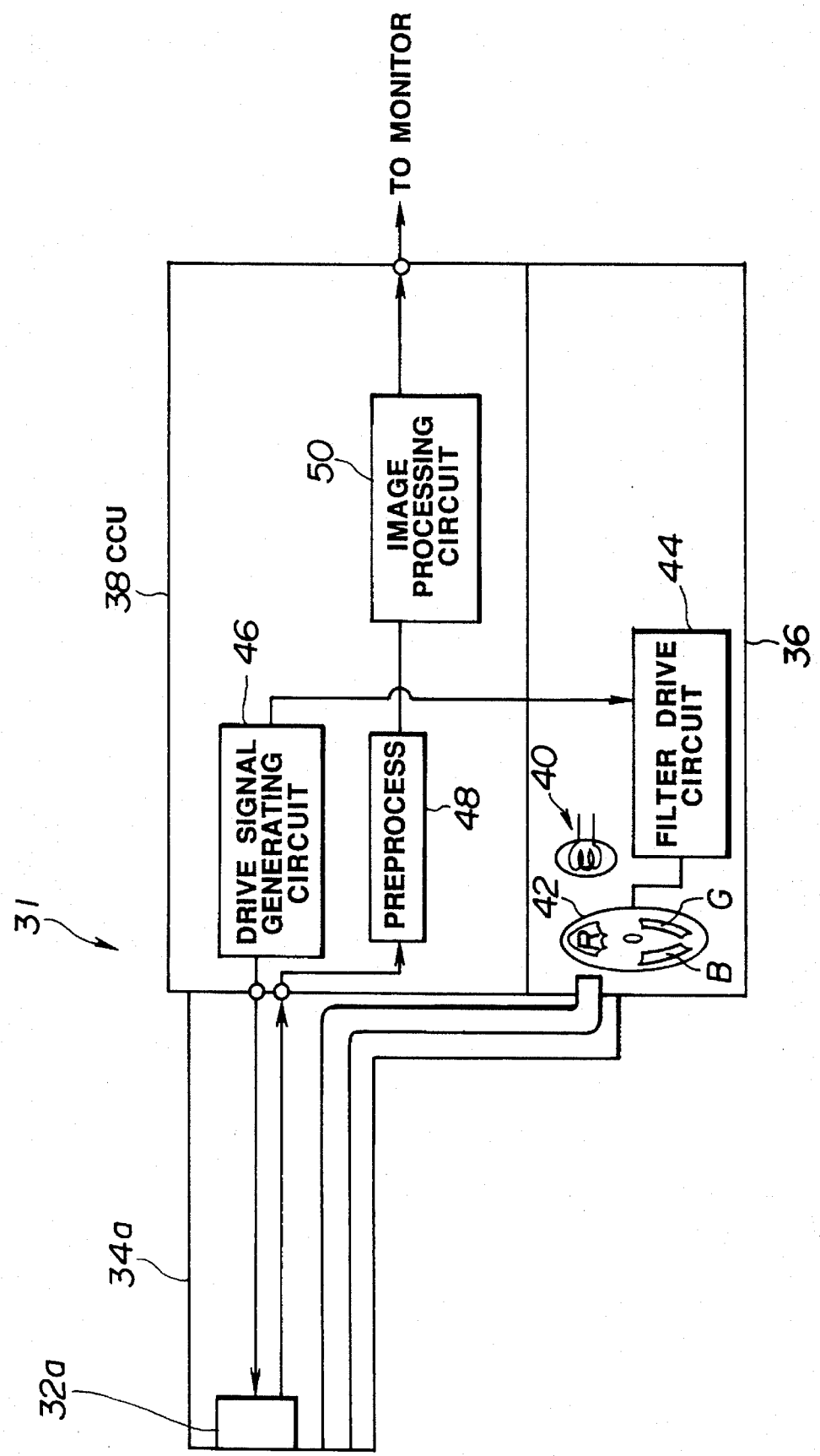
FIGS. 5 to 8 relate to a third embodiment of the invention, FIG. 5 being an arrangement view showing an arrangement of an endoscope system.

As shown in FIG. 5, the endoscope system 31 is a solid image pickup element for picking up a subject image. For example, the endoscope system 31 comprises an endoscope 34a provided with a CCD-(A) 32a, a light source unit 36 for supplying an illuminating light to the endoscope 34a, a camera control unit (CCU) 38 for driving the CCD-(A) 32a within the endoscope 34a to signal-process an image pickup signal, and a monitor (not shown) for displaying, for example, the subject image by an image signal produced by the CCU 38.

The light source unit 36 is provided with a lamp 40 for supplying a white light, an RGB rotary filter 42 for color-separating the while light from the lamp 40 into a plurality of lights having respective wavelengths thereof, for example, RGB, and a filter drive circuit 44 for rotatively driving the RGB rotary filter 42.

The CCU 38 comprises a drive-signal generating circuit 46 for generating a drive signal which drives the CCD-(A) 32a, a preprocess circuit 48 driven by the drive-signal generating circuit 46 for converting the image pickup signal produced by the CCD-(A) 32a, to an image signal, and an image-signal processing circuit 50 for signal-processing an image signal produced by the preprocess circuit 48. In this connection, the drive-signal generating circuit 46 is arranged so as to drive the CCD-(A) 32a and to control the filter drive circuit 44 within the light source unit 36 in synchronism with the drive signal.

Figure 6:
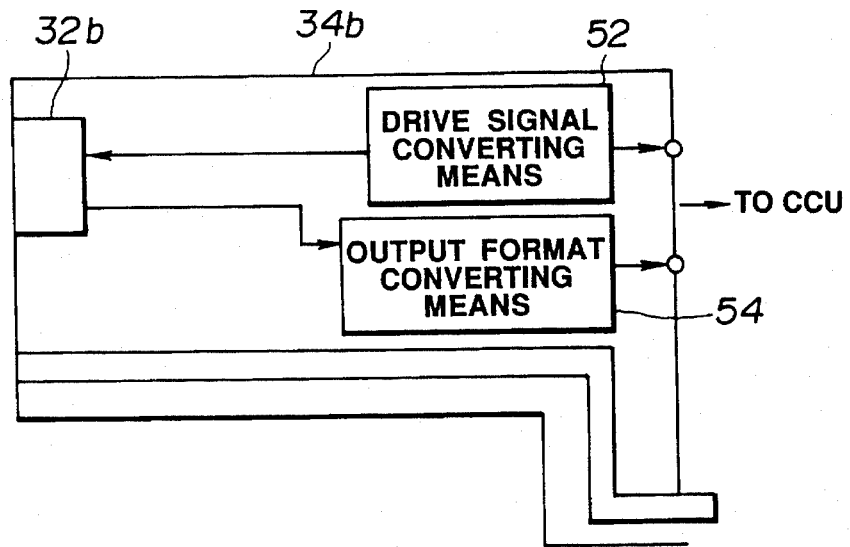

Furthermore, the endoscope system 31 is arranged such that an endoscope 34b illustrated in FIG. 6 is connected to the CCU 38 so as to be capable of forming a system. The endoscope 34b is provided with a CCD-(B) 32b which is different in type from the CCD-(A) 32a. Moreover, the endoscope system 31 is so arranged as to comprise drive-signal converting means 52 for converting the drive signal from the drive-signal generating circuit 46 to a drive signal driving the CCD-(B) 32b, and output-format converting means 54 for converting an image pickup signal from the CCD-(B) 32b driven by the drive-signal converting means 52, to an input format of the preprocess circuit 48.

Figure 7:
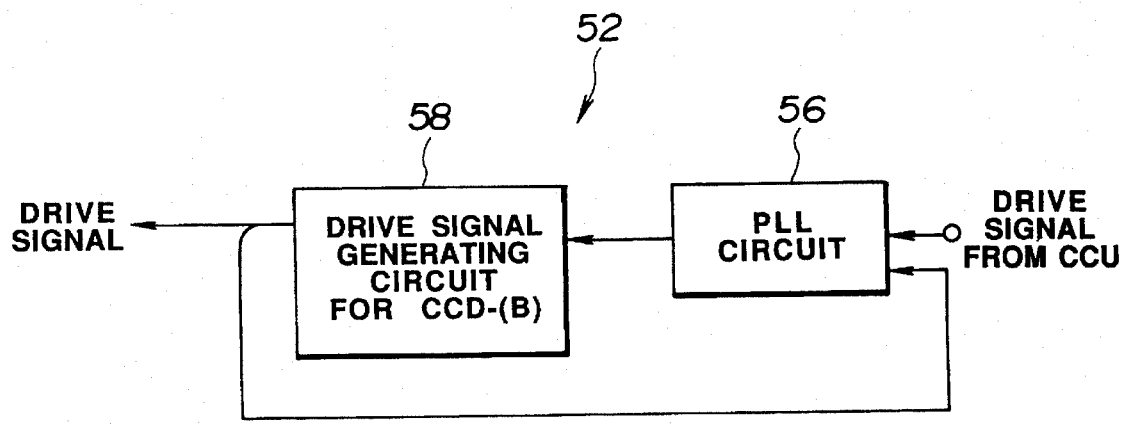

As shown in FIG. 7, the drive-signal converting means 52 comprises a PLL circuit 56 into which the drive signal from the CCU 38 and a drive signal for the CCD-(B) to be described subsequently are Inputted, for synchronizing a phase, and a drive-signal generating circuit 58 for the CCD-(B) into which a clock synchronized with the drive signal from the CCU 38 outputted from the PLL circuit 56 is inputted, for generating a drive signal for the CCD-(B), which is suitable for the CCD-(B) 32b.

Figure 8:
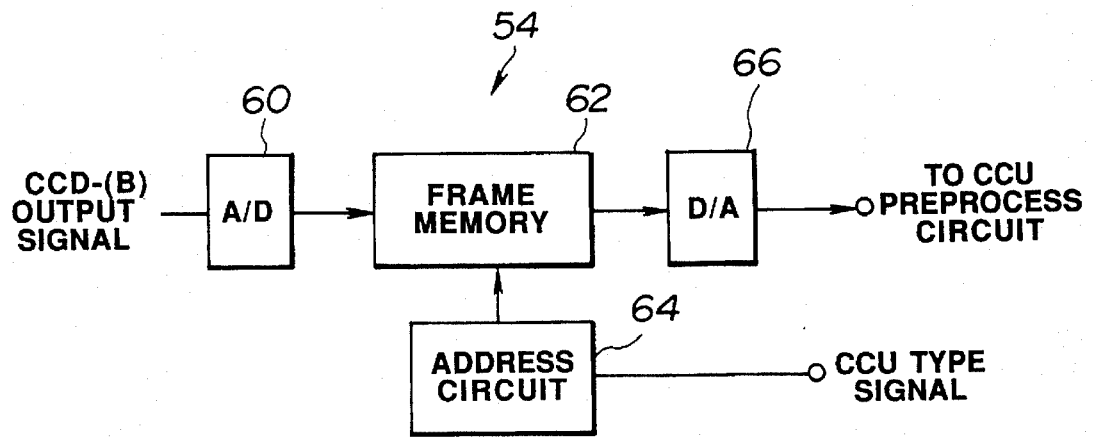

As shown in FIG. 8, the output-format converting means 54 comprises an A/D converter 60 for A/D-converting the image pickup signal from the CCD-(B) 32b, a frame memory 62 for storing therein a quantity corresponding to one frame of the output from the CCD, for example, through the A/D converter 60, a D/A converter 66 for D/A-converting a signal read out from the memory frame 62, and an address circuit 64 of an output type suitable for the type of the CCU, into which a CCU type signal indicating a type of CCU outputted from the CCU 38 is inputted, for issuing or generating an indication so as to thin an output signal from the CCD, or to Interpolate the same, for example.

In the endoscope system 31 arranged as described above, since the CCU 38 executes signal processing corresponding to the CCD-(A) 32a, it is needless to say that it is possible that the endoscope 34a provided with the CCD-(A) 32a is connected to the endoscope system 31. Further, even in the endoscope 34b provided with the CCD-(B) 32b, the drive signal from the CCU 38 is converted to a drive signal corresponding to the CCD-(B) 32b to drive the CCD-(B) 32b so that the image pickup signal from the CCD-(B) 32b is converted to a signal of type corresponding to the CCU 38 by the output-format converting means 54, to thereby output the converted signal.

Accordingly, in the endoscope system 31 according to the present embodiment, only interposition of the signal converting means makes it possible to connect the plurality of electronic endoscopes provided respectively with the CCDs different in type from each other, to a camera control unit corresponding to at least one of the CCDs different in type from each other, and to use the endoscope system 31. In this manner, since the endoscopes provided respectively with the CCDs different in type from each other can be used simply, the existent CCU is used whereby it is possible to realize the endoscope system which is capable of using the plurality of endoscopes coincident with an object, at low cost.

Figure 9:
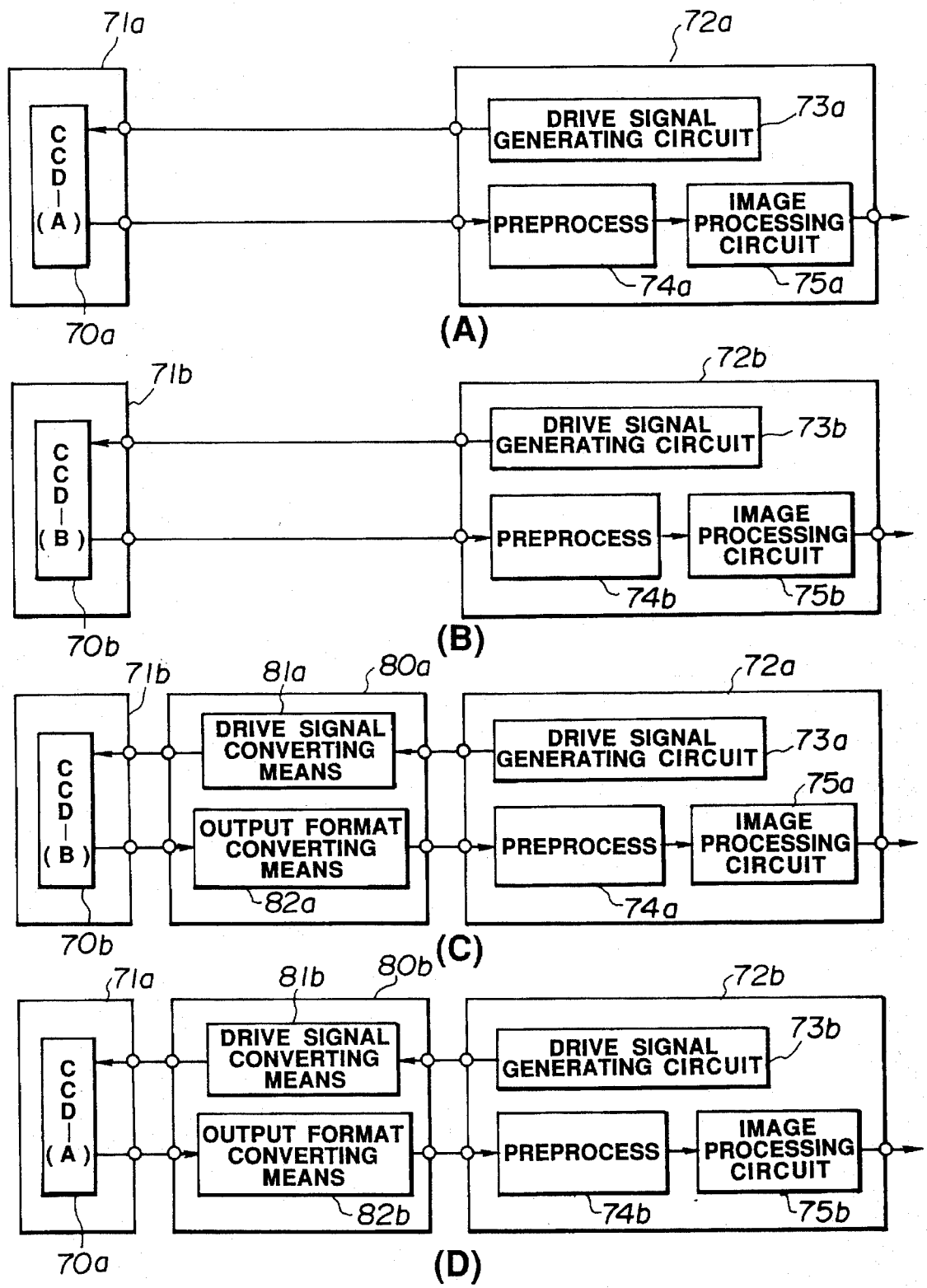
FIG. 9 is an arrangement view of a modification of the third embodiment, in a case where drive-signal converting means and output-format converting means are provided separately from an endoscope and a CCU.

In connection with the above, the embodiment has been arranged such that the drive-signal converting means and the output-format converting means are integrally arranged in the endoscope. However, the embodiment should not be limited to this specific arrangement. As shown in FIG. 9, the drive-signal converting means and the output-format converting means may be arranged separately from the endoscope and the CCU.

That is, an endoscope system comprising, as shown in FIG. 9(A), an endoscope apparatus provided with an endoscope 71a provided with a CCD-(A) 70a, and a drive-signal generating circuit 73a corresponding to the CCD-(A) 70a and a CCU 72a having a preprocess circuit 74a and a signal processing circuit 75a, and, as shown in FIG. 9(B), an endoscope apparatus provided with a drive signal generating circuit 73b corresponding to a CCD-(B) 70b and a CCU 72b having a preprocess circuit 74b and a signal processing circuit 75b, wherein, in a case where an endoscope 71b and the CCU 72a are used to use the endoscope system, as shown in FIG. 9(C), a first converting unit 80a is arranged between an endoscope 71b and a CCU 72a.

In the first converting unit 80a, the drive signal from a CCU 72a is converted to a drive signal taking measures against a CCD-(B) 70b, by a drive-signal converting means 81a to drive the CCD-(B) 70b, so that the image pickup signal from the CCD-(B) 70b is converted to a signal of a type taking measures against the CCU 72a by an output format converting means 82a, to output the latter signal.

Further, in a case where an endoscope 71a and a CCU 72b are used, as shown in FIG. 9(D), a second converting unit 80b is arranged between the endoscope 71a and the CCU 72b. In this second converting unit 80b, the drive signal from the CCU 72b is converted to the drive signal taking measures against a CCD-(A) 70a by a drive-signal converting means 81b to drive the CCD-(A) 70a, so that the image pickup signal from the CCD-(A) 70a is converted to an image pickup signal of type taking measures against the CCU 72b by an output-format converting means 82b, to output the converted signal.

In this manner, the converting units are arranged correspondingly respectively to the plurality of types of the CCUs and the plurality of types of endoscopes, whereby only combination of the existent CCUs and the existent endoscopes with each other makes it possible to use the plurality of types of endoscopes. Thus, an endoscope system taking measures against the plurality of types of endoscopes can be realized at low cost.

By the way, an automatic modulated-light means of the endoscope apparatus has conventionally been arranged by a single kind of time-constant circuit and a single kind of gain circuit. Accordingly, there is a case where normal operation is impossible for CCDs different in number of picture elements from each other, and there is a problem that it is impossible to take measures against a plurality of types of CCDs.

Figure 10:
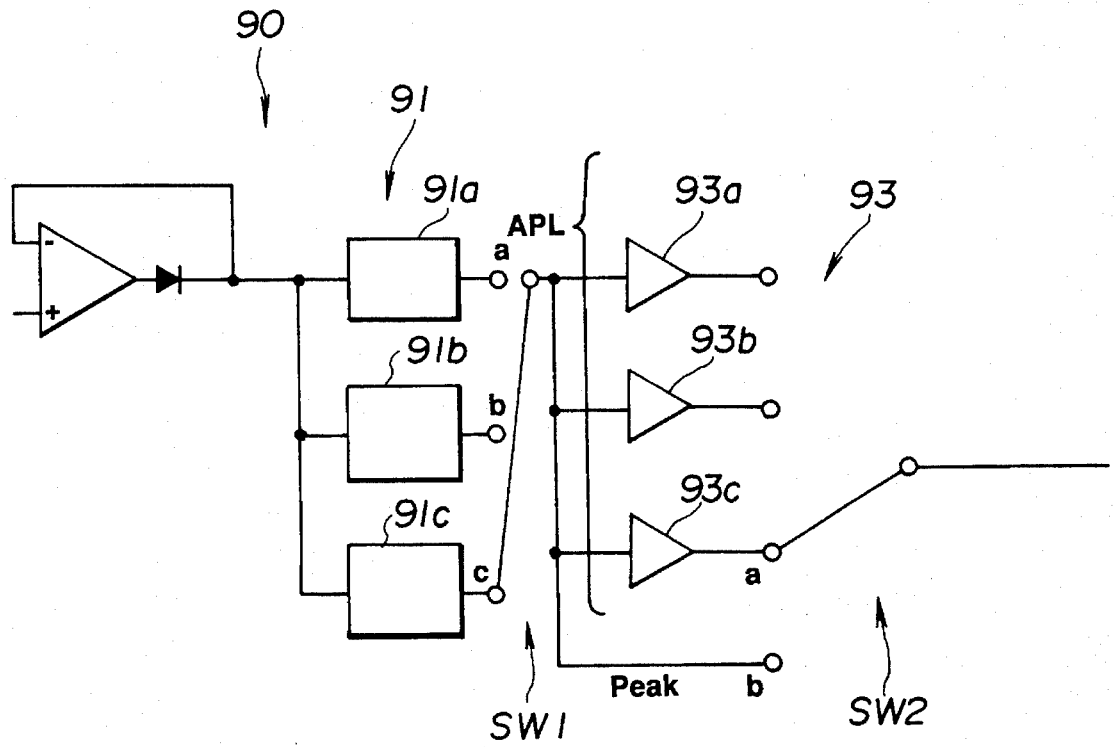
FIG. 10 is an arrangement view showing an arrangement of an automatic modulated-light detection circuit.

In view of the above, as shown in FIG. 10, in an automatic modulated-light detection circuit 90, a Peak/APL time-constant switching circuit 91 and a gain switching circuit 93 capable of switching characteristics in taking measures against a plurality of types of, for example, three types of CCDs are provided, whereby it is possible to solve the above-discussed problem.

The Peak/APL time-constant switching circuit 91 has time-constant circuits 91a, 91b and 91c corresponding respectively to the CCDs, which are switched by a SW1. Moreover, the gain switching circuit 93 has gain circuits 93a, 93b and 93c corresponding respectively to the CCDs, which are switched by a SW2.

In the automatic modulated-light detection circuit 90 arranged in this manner, the Peak/APL time-constant switching circuit 91 and the gain switching circuit 93 can be switched in accordance with the CCDs. Accordingly, there can be produced an advantage that normal operation is always possible with respect also to the CCDs different in number of picture elements from each other.

Figure 11:
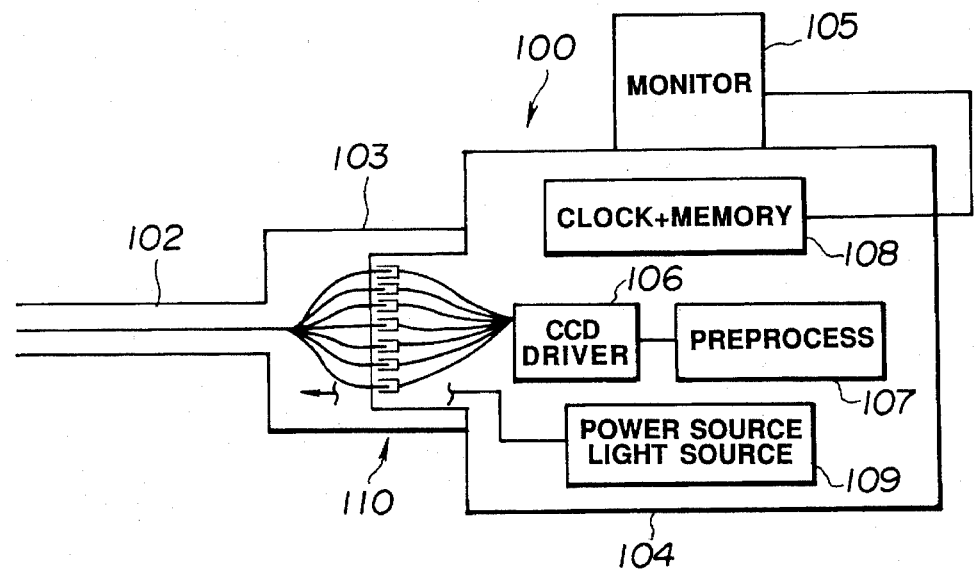
FIG. 11 is an arrangement view showing an arrangement of an endoscope apparatus which is provided with CCD drive control means within a signal processing unit.

Furthermore, as shown in FIG. 11, a conventional endoscope apparatus 100 comprises, for example, a universal cable 102 connected to an endoscope (not shown) for transmitting an illuminating light and various signals for drivingly controlling CCDs to the endoscope, a signal processing unit 104 connected to the universal cable 102 for controlling the endoscope to signal-process the image pickup signal, and a monitor 105 for displaying the image signal from the signal processing unit. The signal processing unit 104 is provided with a electric power source/light source unit 109, a CCD driver circuit 106 and a preprocess circuit 107 for generating various signals for drivingly controlling the CCDs to signal-process the image pickup signal, and a clock memory circuit 108 for storing therein the image pickup signal produced by signal processing of the image pickup signal and for generating a clock that is a reference signal of various circuits.

Connection between the universal cable 102 and the signal processing unit 104 is normally executed by a connector 103 which is provided at a proximal end of the universal cable 102. The number of contacts of connecting portions within the connector 103 is of the order of twelve (12) in sum including one for a GND wire, one for a VDD, two for clock, four for vertical clock, one for reset, one for VOU, and two for other signal lines. Thus, there are a great number of connects, and the connector 103 is weak in electrostatic noise. Further, of these signal lines, there is a signal line directly connected to the CCDs. In order to prevent breakage or damage of the CCDs from occurring, the arrangement is adopted in which a contact is arranged within a recess 110 in the connector 103, so that fingers or the like are in contact with the contact. For this reason, even if waterproof means is applied to connection between the connector 103 and the signal processing unit 104, it is impossible to perfectly wipe out remaining water within the recess 110. Thus, there is also a problem that it is substantially impossible to execute water tightness or waterproofness.

Figure 12:
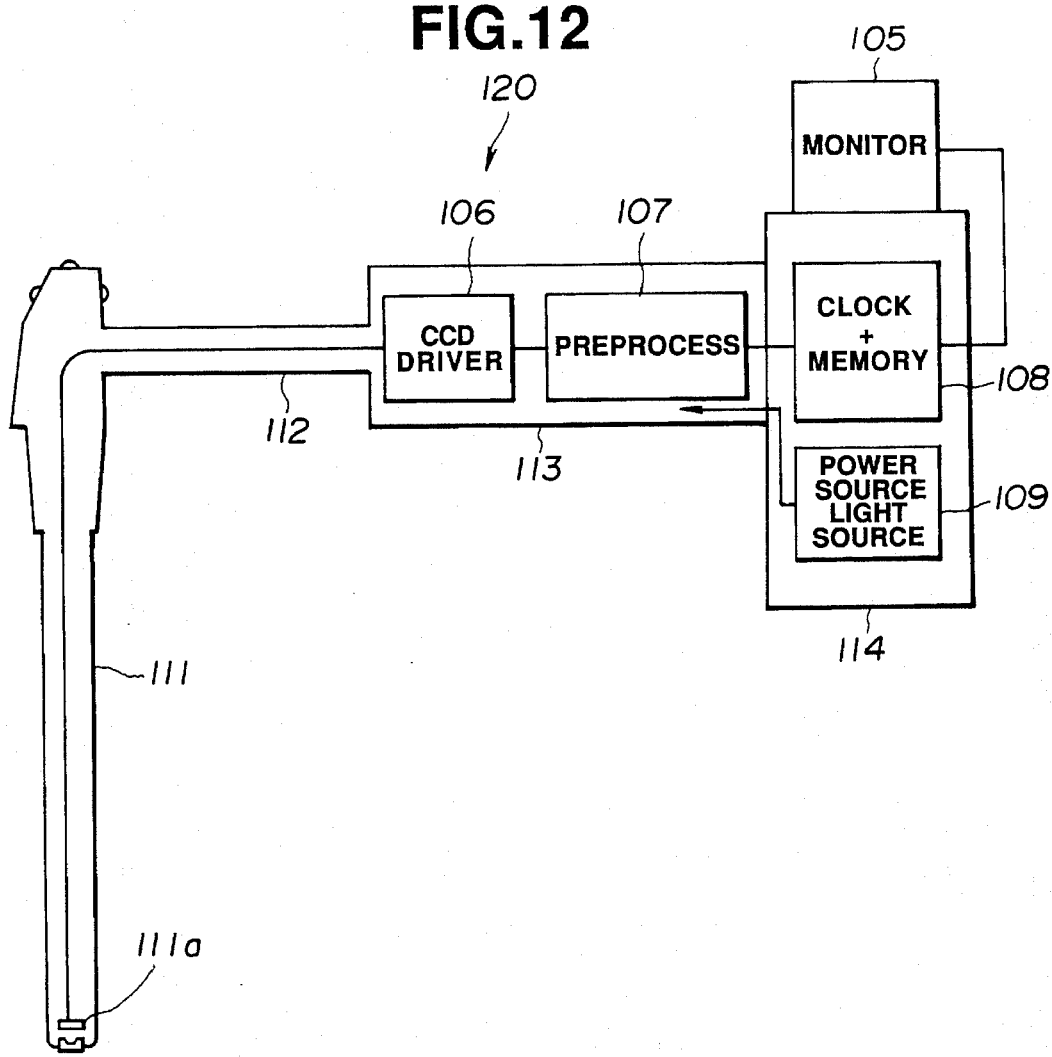
FIG. 12 is an arrangement view showing an arrangement of the endoscope apparatus which is provided with the drive control means within a connector for a connecting cable.

In view of the above, in an endoscope apparatus 120 shown in FIG. 12, a CCD driver circuit 106 for driving a CCD 111a within an endoscope 111 and a preprocess circuit 107 are arranged within a connector 113 which is provided at a forward end of a universal cable 112. A signal processing unit 114 is arranged by a clock memory circuit 108 and a power source/light source unit 109, whereby the above-discussed problem tends to be solved.

With the endoscope apparatus 120 arranged as described above, the number of contacts at the connection between the signal processing unit 114 and the connector 113 is brought to an extent of five (5) in sum including one of GND line, one of VDD, one of clock, two of VOUT and the like, for example. Thus, it is possible to reduce the number of contacts considerably as compared with the conventional number. Further, a signal line directly connected to the CCD 111a can be processed within the connector 113, and is not exposed to the outside. Accordingly, a structure of the connection is simplified. The connection can be arranged only by electrostatic-proof contacts, it is not required or unnecessary to provide a recess in the connection. Thus, there can be produced an advantage that perfect waterproofing is realized.

In connection with the above, in the endoscope apparatus 120, the arrangement of the signal processing unit 114 are only the clock memory circuit 108 and the power source/light source unit 109. Accordingly, even in an endoscope provided with CCDs which are different in structure or in driving system, a CCD driver circuit taking measures against the CCDs and the preprocess circuit are arranged within the connector, whereby the endoscope provided with CCDs different in structure or in driving system from each other can be connected to the signal processing unit 114. Thus, there can also be produced an advantage that it is possible to arrange an endoscope apparatus having a wide use.

Figure 13:
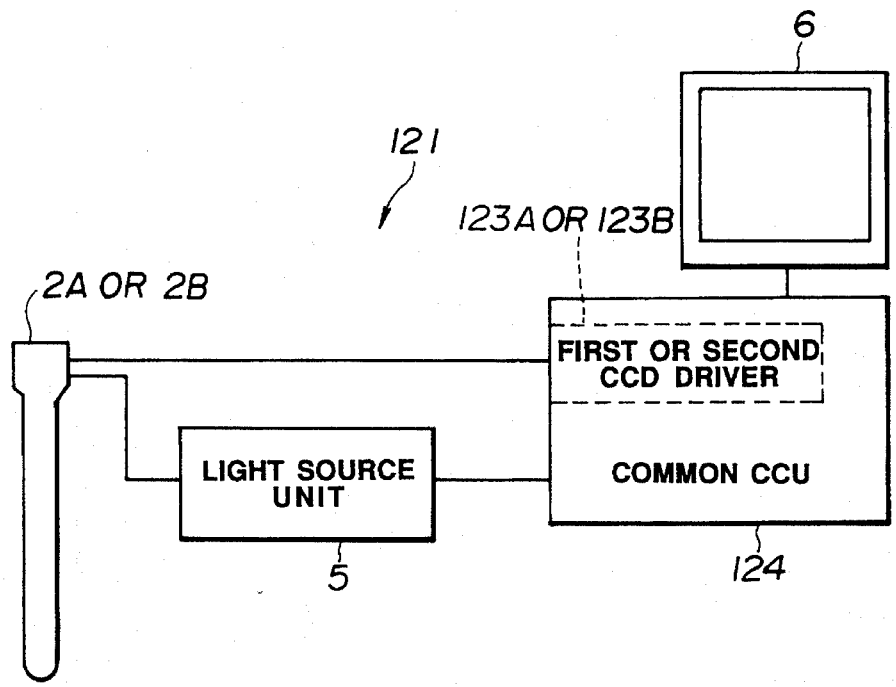
FIGS. 13 and 14 relate to a fourth embodiment of the invention, FIG. 13 being a block diagram showing an arrangement of an endoscope system.
Figure 14:
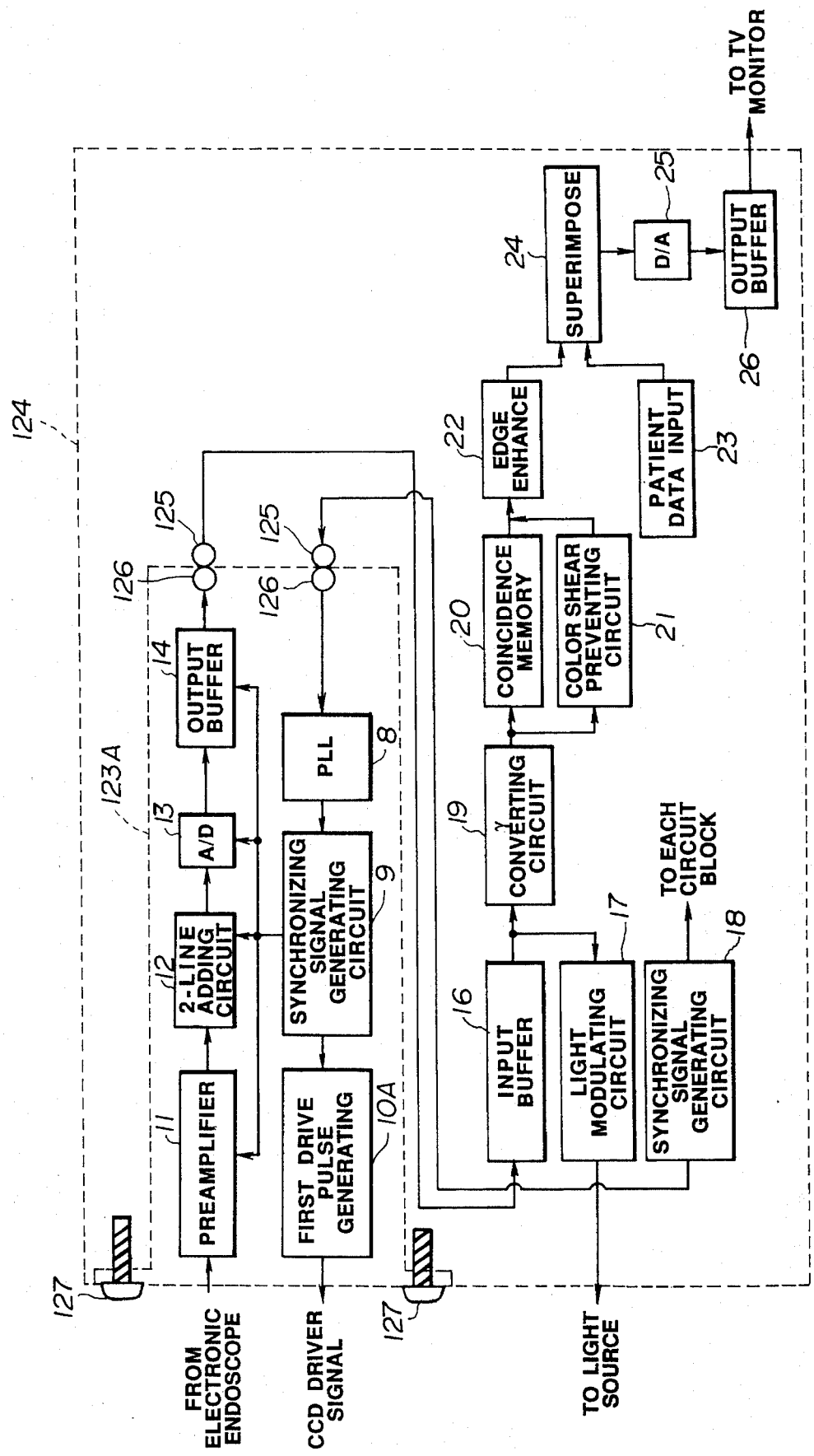

FIGS. 13 and 14 show a fourth embodiment of the invention.

The fourth embodiment is an example in which the CCD driver in the first embodiment is provided detachably so as to be integrated with respect to a common CCU.

Figure 18:
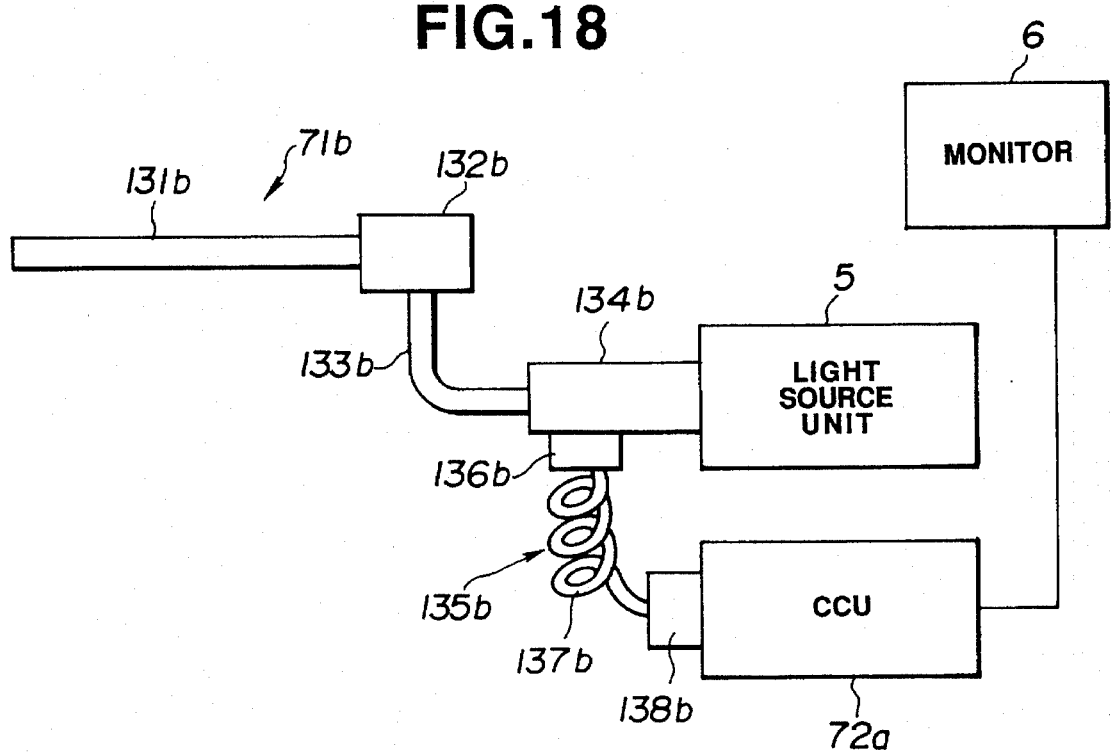

As shown in FIG. 18, an endoscope system 121 is provided with the common CCU 4 in the first embodiment and a common CCU 124 capable of coping with a plurality of types of endoscopes having similar functions. A first CCD driver 123A taking measures against the first electronic endoscope 2A, or a second CCD driver 123B taking measures against the second electronic endoscope 2B are detachably built-in-connected to the common CCU 124. That is, the first CCD driver 123A or the second CCD driver 123B is arranged in appearance as a single unit together with the common CCU 124 under a condition connected to the common CCU 124.

Moreover, the common CCU 124 executes normal exchanges of signals with respect to the first CCD driver 123A when the first CCD driver 123A is connected, and with respect to the second CCD driver 123B when the second CCD driver 123B is connected, and executes signal processing and driving of the CCDs corresponding to the first electronic endoscope 2A or the second electronic endoscope 2B. Other arrangements are similar to those of the first embodiment, and the description thereof will be omitted.

FIG. 14 shows an internal arrangement at the time the first CCD driver 123A is built-in-connected to the common CCU 124. The common CCU 124 and the first CCD driver 123A are provided with electric contacts 125 and 126, respectively. At the built-in-connection, the electronic contacts 125 and 126 are connected to each other to send and receive a signal. Moreover, the first CCD driver 123A is mechanically fixed to a casing of the common CCU 124 by fixing means 127 consisting of screws or the like.

The fixing means 127 is demounted whereby it is possible to mount and demount the first CCD driver 123A on and from the common CCU 124. In a case where the second electronic endoscope 2B is used, it is possible that, in place thereof, the second CCD driver 123B is connected to and fixed to the common CCU 124.

In connection with the above, in FIG. 14, the internal arrangement of the first CCD driver 128A is similar in arrangement to the first CCD driver 3A illustrated in FIG. 2(a) regarding the first embodiment, and the functional arrangement of the common CCU 124 is similar in arrangement to the common CCU 4 illustrated in FIG. 3 regarding the first embodiment. Accordingly, the description thereof will be omitted. Moreover, the arrangement at the time the second CCD driver 123B is connected to the common CCU 124 is brought to one in which, in FIG. 14, a portion of the first CCD driver 128A is replaced with an arrangement of the second CCD driver 3B illustrated in FIG. 2(b) regarding the first embodiment.

In this manner, the CCD drivers corresponding respectively to the plurality of different CCDs are detachably built-in-connected selectively to the common CCU, whereby it is possible to arrange a system suitable for the scope used similarly to the first embodiment easily and at low cost. Furthermore, under the condition that the CCD driver is connected to the common CCU, the CCUs are brought to an integral arrangement. Accordingly, the arrangement of the system can be simplified, and reception, conveyance, operability and so on are improved.

Figure 15:
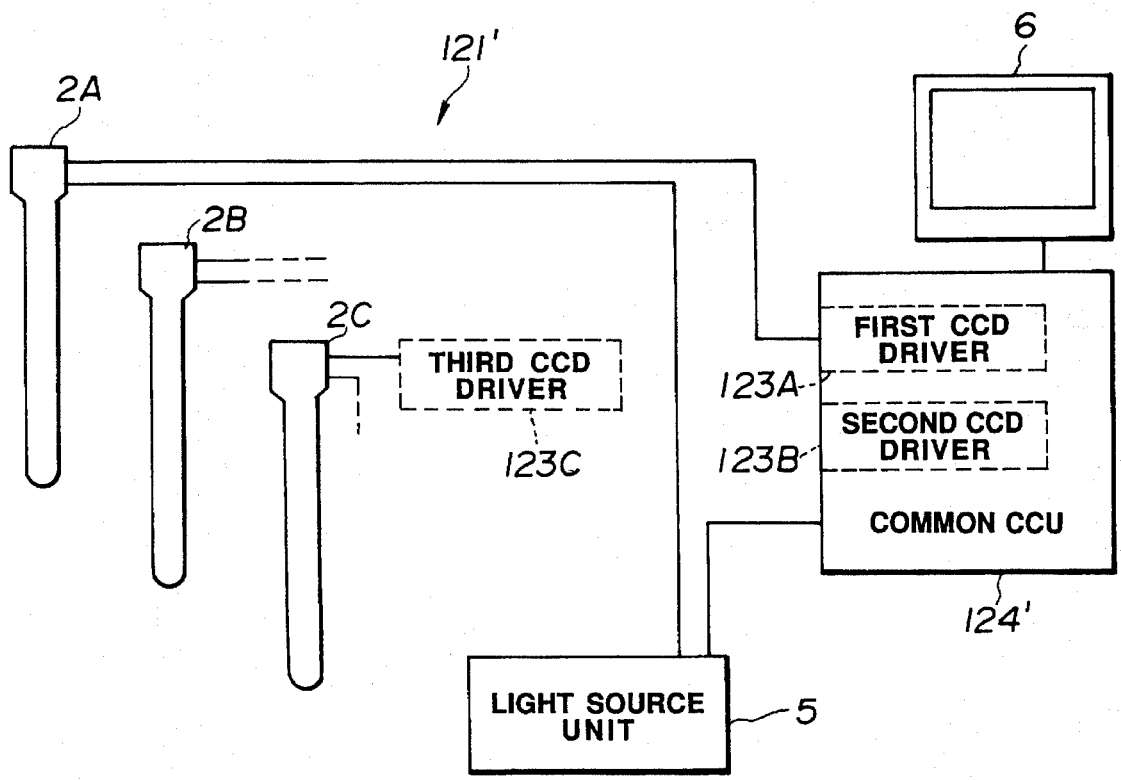
FIG. 15 is a block diagram showing an arrangement of an endoscope system according to a modification of the fourth embodiment according to the invention.
Figure 16:
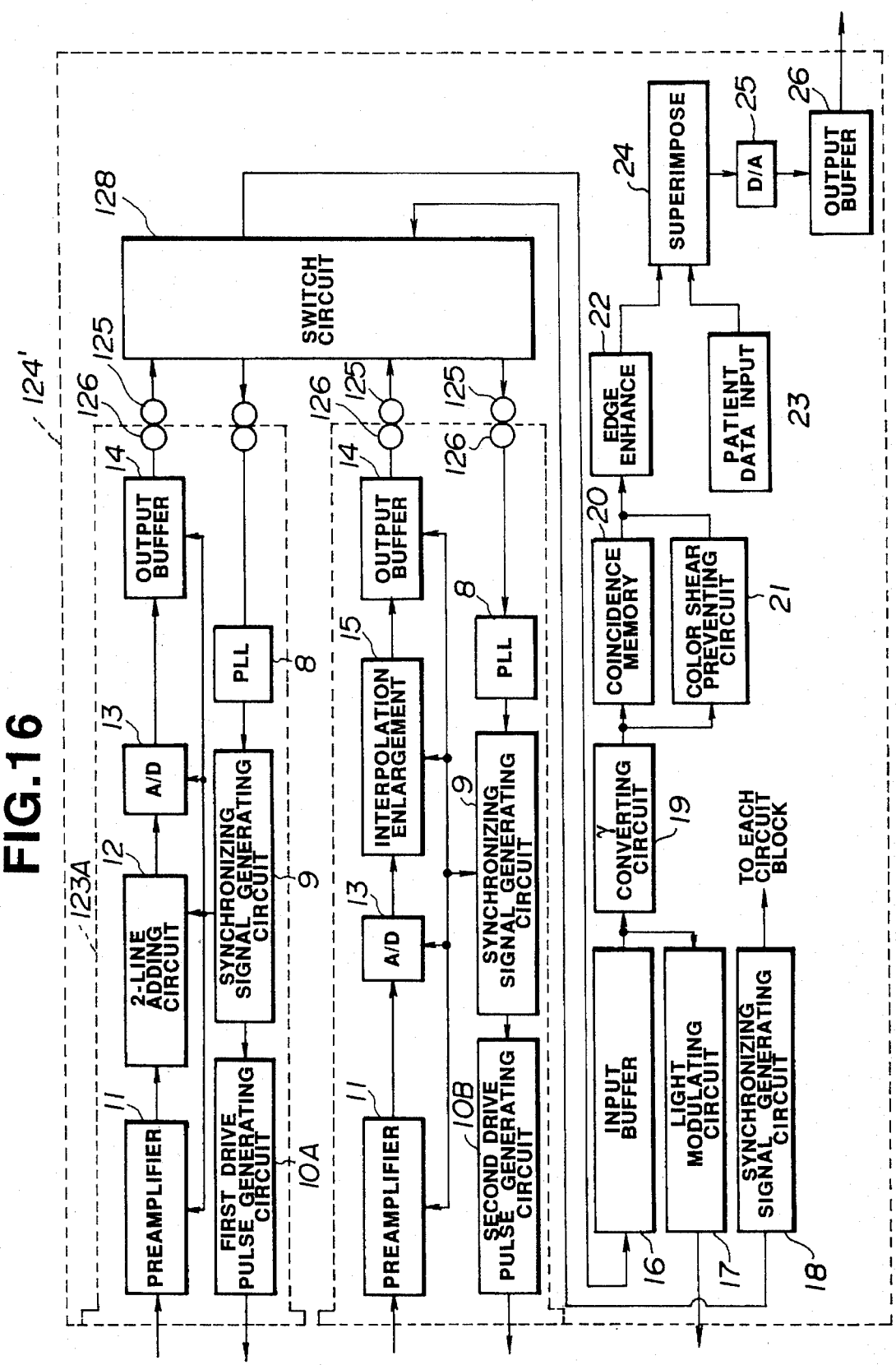
FIG. 16 is a block diagram showing an internal arrangement of the endoscope system illustrated in FIG. 15.

FIGS. 15 and 16 show a modification of the fourth embodiment of the invention.

An endoscope system 121' in the modification is an example in which a plurality of (two in the figure) CCD drivers can be built-in-connected selectively and detachably to a common CCU 124'.

CCDs different in specification from each other are arranged within electronic endoscopes 2A, 2B and 2C, and are connected respectively to a first CCD driver 123A, a second CCD driver 123B and a third CCD driver 123C which correspond respectively to the CCDs, so that driving of the CCDs and signal processing in a previous stage are executed. Optionally two of the CCD drivers 123A, 123B and 123C can detachably be built-in-connected to the common CCU 124'. The connected CCD drivers are mechanically fixed by fixing means 127, similarly to the arrangement in FIG. 14. In this connection, other arrangements are similar to those of the fourth embodiment.

An internal arrangement at the time the first CCD driver 123A and the second CCD driver 123B are built-in-connected to the common CCU 124' is shown in FIG. 16. In this connection, in FIG. 16, the respective arrangements of the first CCD driver 123A and the second CCD driver 123B and the functional arrangement of the common CCU 124' are similar to those of the fourth embodiment.

The common CCU 124' is provided with a switch circuit 128 which selectively switches a CCD driver built-in-connected, and an input line to the input buffer 16 and an output line from a synchronizing-signal generating circuit 18 are connected to one of the CCD drivers. An electric contact 125 is connected to the other of the switch circuits 128. The switch circuit 128 is so arranged as to be selectively switched to either one of the two CCD drivers connected through the electric contacts 125 and 126, manually or the like.

In connection with the above, the CCD drivers 123A, 123B and 123C may either be detachable with respect to the common CCU 124'. Further, any one of the CCD drivers 123A, 123B and 123C may be such an arrangement as to be fixedly connected to the common CCU 124' so that the arrangement is detachable.

With the arrangement in this manner, the embodiment can take measures against a plurality of types of endoscopes provided with CCDs different in specification from each other, similarly to the fourth embodiment.

Figure 17:
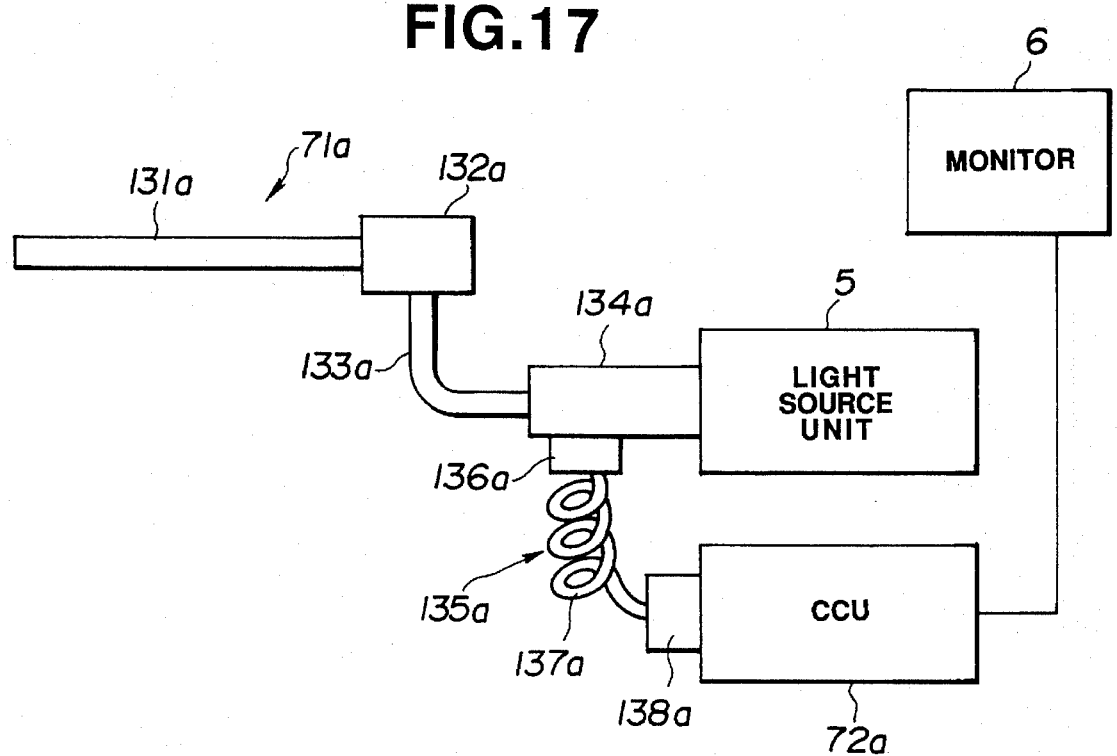
FIGS. 17 and 18 relate to a fifth embodiment of the invention, FIG. 17 being a block diagram showing an arrangement of an endoscope system.

FIGS. 17 and 18 show a fifth embodiment of the invention.

Similarly to the modification of the third embodiment illustrated in FIG. 9, the fifth embodiment is an example in which drive-signal converting means and output-format converting means are provided separately from the endoscope and the CCU.

As shown in FIG. 17, an endoscope 71a is connected to a light source unit 5 and a CCU 72a so that an observing image of a subject image picked-up by the endoscope 71a is displayed on a monitor 6.

The endoscope 71a is arranged such that the endoscope 71a has an elongated inserting section 131a, and an operating section 132a thick in diameter, and a connector portion 134a is provided at an end of a universal cord 133a extending from a side of the operating section 132a. A connecting cable 135a is detachably connected to the side of the connector portion 134a so that the connector portion 134a is connected directly to the light source unit 5, and is connected to the CCU 72a through the connecting cable 135a.

The connecting cable 135a is arranged such that a connector 136a on the scope side connectable to the connector portion 134a, an expandable curl cable portion 137a in which a signal line is inscribed, and a connector 138a on the CCU side connectable to the CCU 72a are provided in connection. The connector 136a on the scope side is detachably connected to the connector portion 134a, while the connector 138a on the CCU side is detachably connected to the CCU 72a.

Similarly to that in FIG. 9, a CCD-(A) 70a is provided at the forward end of the inserting section 131a of the endoscope 71a. An illuminating light from the light source unit 5 is outgone from the forward end of the inserting section 131a through a light guide (not shown) inserted into the endoscope 71a. An image of the illuminated subject is picked up by the CCD-(A) 70a. An image pickup signal from the CCD-(A) 70a is inputted to the CCU 72a through the universal code 133a and the connecting cable 135a. Various signals are processed in the CCU 72a so that an observing image is displayed on the monitor 6.

On the other hand, in a case where the endoscope 71b provided with a CCD-(B) 70b is connected, a system is arranged as illustrated in FIG. 18. The endoscope 71b is connected to a light source unit 5 through a universal code 133b and a connector portion 134b, and is connected to a CCU 72a through a connecting cable 135b. Here, an electric circuit including the drive-signal converting means 81a illustrated in FIG. 9(C) and the output-format converting means 82a is provided at the connecting cable 135b, and has a function of the first converting unit 80a. That is, the endoscope system illustrated in FIG. 18 is a functional arrangement similar to that in FIG. 9(C), and takes a form in which the first converting unit 80a is provided within the connecting cable 135b.

In this manner, the converting unit is provided within the connecting cable connected to the CCU, whereby, similarly to the third embodiment, it is possible to use the existent CCU and the plurality of types of endoscopes in combination with each other easily.

Figure 19:
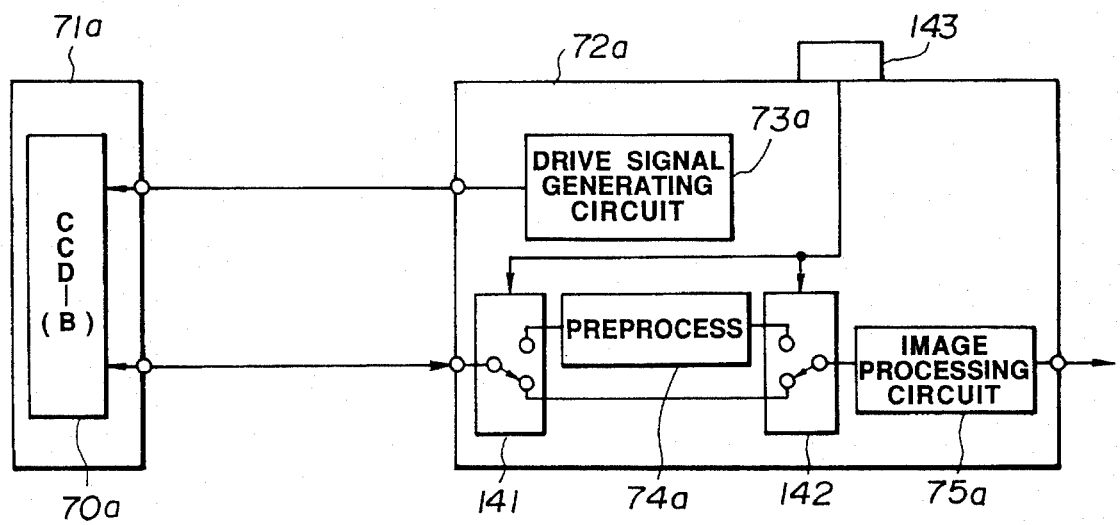
FIGS. 19 and 20 relate to a sixth embodiment of the invention, FIG. 19 being a block diagram showing an arrangement of an endoscope system.
Figure 20:
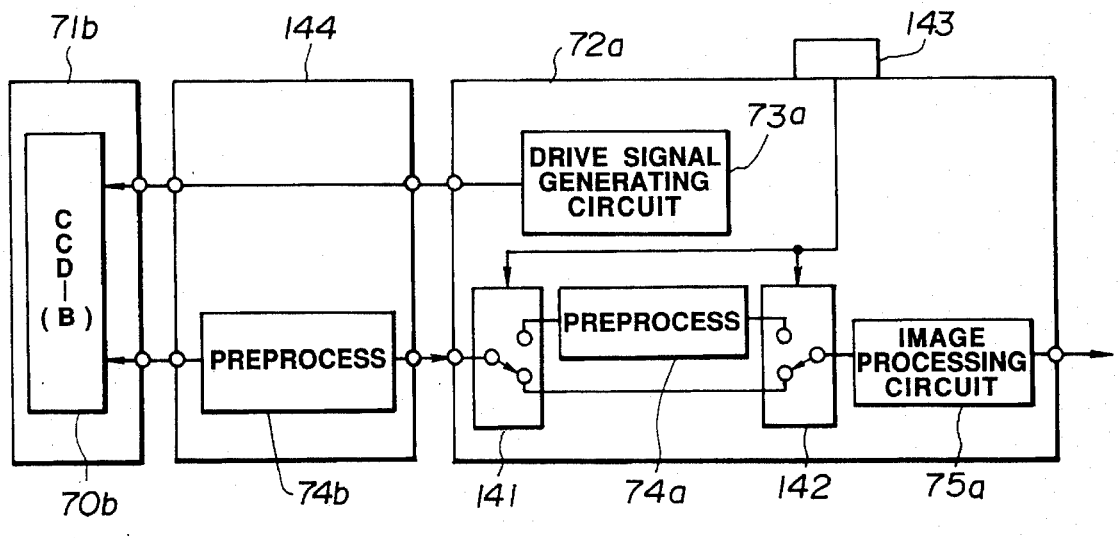

FIGS. 19 and 20 show a sixth embodiment of the invention.

Similarly to the modification of the third embodiment illustrated in FIG. 9, the sixth embodiment is also an example in which signal converting means capable of taking measures against CCDs different in specification from each other is provided separately from the endoscope and the CCU. In this connection, an arrangement of a portion converting the image pickup signal from the CCD to a signal taking measures against an input form of common signal processing circuit at a later stage will be described here. Conversion of the drive signal from the CCD is substantially similar that in the fifth embodiment, and the description will be omitted.

As shown in FIG. 19, the endoscope system according to the present embodiment is provided with switch circuits 141 and 142 for switching whether a preprocess circuit 74a is connected to a circuit, or the preprocess circuit 74a is bypassed so as to be passed through, in front of and in rear of the preprocess circuit 74a, in addition to the arrangement illustrated in FIG. 9(A). These switch circuits 141 and 142 can be switched by a change-over switch 143. Other arrangements are similar to those illustrated in FIG. 9(A).

In a case where an endoscope 71a provided with a CCD-(A) 70a is used, the switch circuits 141 and 142 are switched such that the endoscope 71a is connected directly to a CCU 72a, and the output end of the CCD-(A) 70a is connected to the preprocess circuit 74a corresponding to the CCD-(A) 70a by the change-over switch 143.

On the other hand, in a case where the endoscope 71b provided with the CCD-(B) 70b is used, a system is arranged as shown in FIG. 20. That is, a converting unit 144 for converting the image pickup signal from a CCD-(B) 70b so as to correspond to a CCU 72a is connected to a location between a endoscope 71b and the CCU 72a. The converting unit 144 is provided with a preprocess circuit 74b corresponding to the CCD-(B) 70b, and is connected to the output end of the CCD-(B) 70b. At this time, the switch circuits 141 and 142 are switched by a change-over switch 143 so as to be bypassed through the preprocess circuit 74a.

With the arrangement described above, in a case where the endoscope 71a is connected, an output signal from the CCD-(A) 70a is signal-processed by the preprocess circuit 74a. In a case where the endoscope 71b is connected, the output signal from the CCD-(B) 70b is signal-processed by the preprocess circuit 74b. Thus, signal processing is executed correspondingly to the CCDs different from each other. By doing so, similarly to the third embodiment, it is possible to easily arrange the system capable of using a plurality of types of endoscopes.

In the invention, it is apparent that different embodiments can be arranged in a wide scope on the basis of the invention without departure from a spirit and a scope of the invention. The invention should not be limited by specific embodiments thereof other than being limited by appended claims.

What is claimed is:

1. An endoscope system comprising:

an endoscope control unit provided with image signal generating means for signal processing an image pickup signal having fixed specifications from an endoscope to generate a standard image signal, and a main signal generating means for generating a main synchronizing signal for driving image pickup means provided on said endoscope;

a first endoscope connectable to said endoscope control unit and provided with high resolution first image pickup means having a large number of pixels, and capable of picking up an image pickup signal having higher resolution than said image pickup signal having said fixed specifications;

a second endoscope connectable to said endoscope control unit and provided with low resolution second image pickup means being miniaturized and capable of picking up an image pickup signal having a lower resolution than an image pickup signal of said fixed specifications;

first signal rationalizing means for rationalizing a form of a signal exchanged between said first endoscope and said endoscope control unit, said first signal rationalizing means including a first subsidiary synchronizing signal generator circuit for detecting the phase of said main synchronizing signal generated from said main synchronizing signal generator circuit to generate a first subsidiary synchronizing signal which is synchronized with said main synchronizing signal, a first drive pulse generator circuit for signal processing said first subsidiary synchronizing signal which is generated from said first subsidiary synchronizing signal generator circuit to generate a first drive signal used for said high resolution first image pickup means, and two-line adding means for simultaneously reading and adding together two lines of the image pickup signal from said high resolution first image pickup means on the basis of said first subsidiary synchronizing signal to provide high-speed reading, said two-line adding means outputting an image pickup signal of said fixed specifications to said image signal generating means; and a second signal rationalizing means for rationalizing a form of a signal exchanged between said second endoscope and said endoscope control unit, said second signal rationalizing means including a second subsidiary synchronizing signal generator circuit for detecting the phase of said main synchronizing signal generated from said main synchronizing signal generator circuit to generate a second subsidiary synchronizing signal which is synchronized with said main synchronizing signal, a second drive pulse generator circuit for signal processing said second subsidiary synchronizing signal from said second subsidiary synchronizing signal generator circuit to generate a second drive signal used for said low resolution second image pickup means, and interpolation enlargement means for interpolation processing an image pickup signal from said low resolution second image pickup means on the basis of said second subsidiary synchronizing signal to provide enlargement of said image pickup signal, said interpolation enlargement means for outputting an image pickup signal of said fixed specifications to said image signal generating means.

2. An endoscope system comprising:

a first endoscope provided with high resolution first image pickup means having a large number of pixels for picking up a subject image as a high resolution image;

a second endoscope smaller in size than said first image pickup means and provided with low resolution second image pickup means;

an endoscope control unit provided with image signal generating means for signal processing an image pickup signal from said low resolution second image pickup means to generate an image signal, and a main drive pulse signal generating means for generating a main drive pulse signal for driving said second image pickup means; and signal rationalizing means for rationalizing a form of a signal exchanged between said first endoscope and said endoscope control unit when said first endoscope is combined with said endoscope control unit, said signal rationalizing means including a subsidiary drive pulse signal generating circuit for detecting the phase of said main drive pulse signal generated from said main drive pulse signal generating means to generate a subsidiary drive pulse signal which is synchronized with said main drive pulse signal and which is used for simultaneously generating two lines of the image pickup signal from said high resolution first image pickup means, and two-line adding means for detecting the phase of said main drive pulse signal and adding together two lines of the image pickup signal simultaneously generated from said high resolution first image pickup means on the basis of said detection of the phase, said two-line adding means outputting the signals added together to said image signal generating means.

* * * * *